United States Patent
Sukovic et al.

(10) Patent No.: US 7,394,888 B2
(45) Date of Patent: Jul. 1, 2008

(54) CT SCANNER FOR LOWER EXTREMITIES

(75) Inventors: Predrag Sukovic, Birmingham, MI (US); Neal Clinthorne, Ann Arbor, MI (US); James A. Bertolina, Portage, MI (US); Miodrag Rakic, Redondo Beach, CA (US); Joseph Webster Stayman, Ann Arbor, MI (US)

(73) Assignee: Xoran Technologies, Inc., Ann Arbor, MI (US)

( * ) Notice: Subject to any disclaimer, the term of this patent is extended or adjusted under 35 U.S.C. 154(b) by 0 days.

(21) Appl. No.: 11/415,856

(22) Filed: May 2, 2006

(65) Prior Publication Data

US 2006/0245539 A1    Nov. 2, 2006

Related U.S. Application Data

(60) Provisional application No. 60/676,734, filed on May 2, 2005.

(51) Int. Cl.
*A61B 6/00* (2006.01)
(52) U.S. Cl. .......................................... 378/20; 378/208
(58) Field of Classification Search .................. 378/20, 378/54, 55, 4, 15, 193–197, 204, 208
See application file for complete search history.

(56) References Cited

U.S. PATENT DOCUMENTS

| | | | |
|---|---|---|---|
| 4,829,549 A * | 5/1989 | Vogel et al. | 378/55 |
| 5,743,264 A | 4/1998 | Bonutti | 600/415 |
| 2002/0193683 A1 | 12/2002 | Danielsson et al. | 600/411 |
| 2005/0053185 A1 | 3/2005 | Sukovic et al. | 378/4 |
| 2005/0053186 A1 | 3/2005 | Sukovic et al. | 378/4 |
| 2006/0020196 A1 | 1/2006 | Elias | 600/407 |

FOREIGN PATENT DOCUMENTS

| | | |
|---|---|---|
| DE | 10146915 | 4/2003 |
| WO | 2005/102173 | 11/2005 |

OTHER PUBLICATIONS

International Search Report and Written Opinion mailed on Sep. 5, 2006.

* cited by examiner

*Primary Examiner*—Courtney Thomas
(74) *Attorney, Agent, or Firm*—Carlson, Gaskey & Olds

(57) ABSTRACT

A CT scanning system provides the ability to scan a patient's lower extremities while the patent is upright, i.e. either standing on the foot, or at least putting some load on the foot, or with the ankle at a given angle. The CT scanning system provides a generally horizontal upper support surface on which the patient's foot is supported. A gantry supporting an x-ray source and x-ray detector are rotated about a z-axis through the support surface. With the CT scanning system, the patient's lower extremities can be scanned while under load.

43 Claims, 5 Drawing Sheets

CT SCANNER FOR LOWER EXTREMITIES

REFERENCE TO RELATED APPLICATION

This application claims priority to U.S. Provisional Application Ser. No. 60/676,734, which was filed on May 2, 2005.

BACKGROUND OF THE INVENTION

Diagnosing foot and ankle injuries and problems can be difficult. A large number of small, overlapping bones in the foot and ankle sometimes obscure the visualization of fractures or other problems from traditional X-rays. As a result, doctors often order CT scans of the foot and ankle. However, current CT scanners are too large, expensive and complicated to be located in the doctor's office. Therefore, the patient must go to a different location for the CT scan and then return to the doctor for analysis. Immediate diagnosis and treatment are often delayed by days.

Additionally, the current CT scanners require the patient to lie down, since they are designed to scan the whole body. The current CT scanner cannot take a CT scan of the foot and ankle under load (i.e., while the patient is standing). For patients that only experience foot or ankle pain when standing, or for whom walking or standing aggravates their foot or ankle pain, it may be desirable to be able to visualize the foot and ankle under load, since many of the bones and tissue in the foot and ankle may shift and move to a different position under load.

SUMMARY OF THE INVENTION

A CT scanning system provides the ability to scan a patient's lower extremities while the patent is upright, i.e. either standing on the foot, or at least putting some load on the foot, or with the ankle at a given angle. The CT scanning system provides a generally horizontal upper support surface on which the patient's foot is supported. A gantry supporting an x-ray source and x-ray detector are rotated about a z-axis through the support surface. With the CT scanning system, the patient's lower extremities can be scanned while under load. Other features and advantages of the CT scanning system are described below.

BRIEF DESCRIPTION OF THE DRAWINGS

Other advantages of the present invention can be understood by reference to the following detailed description when considered in connection with the accompanying drawings wherein.

DETAILED DESCRIPTION OF PREFERRED EMBODIMENTS

Figure 1:
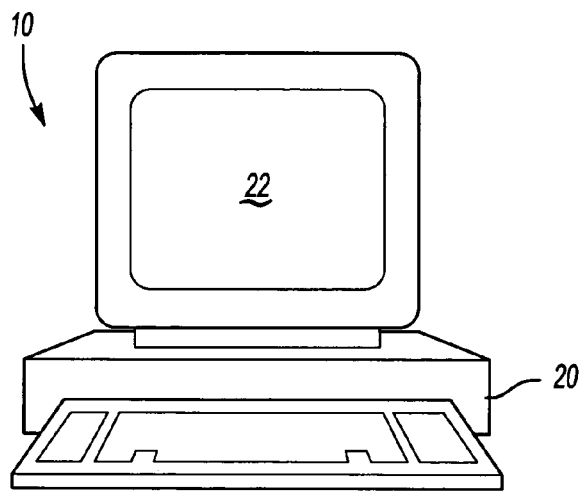
FIG. 1 is a schematic sectional view of a CT scanning system according to one embodiment of the present invention.
Figure 1:
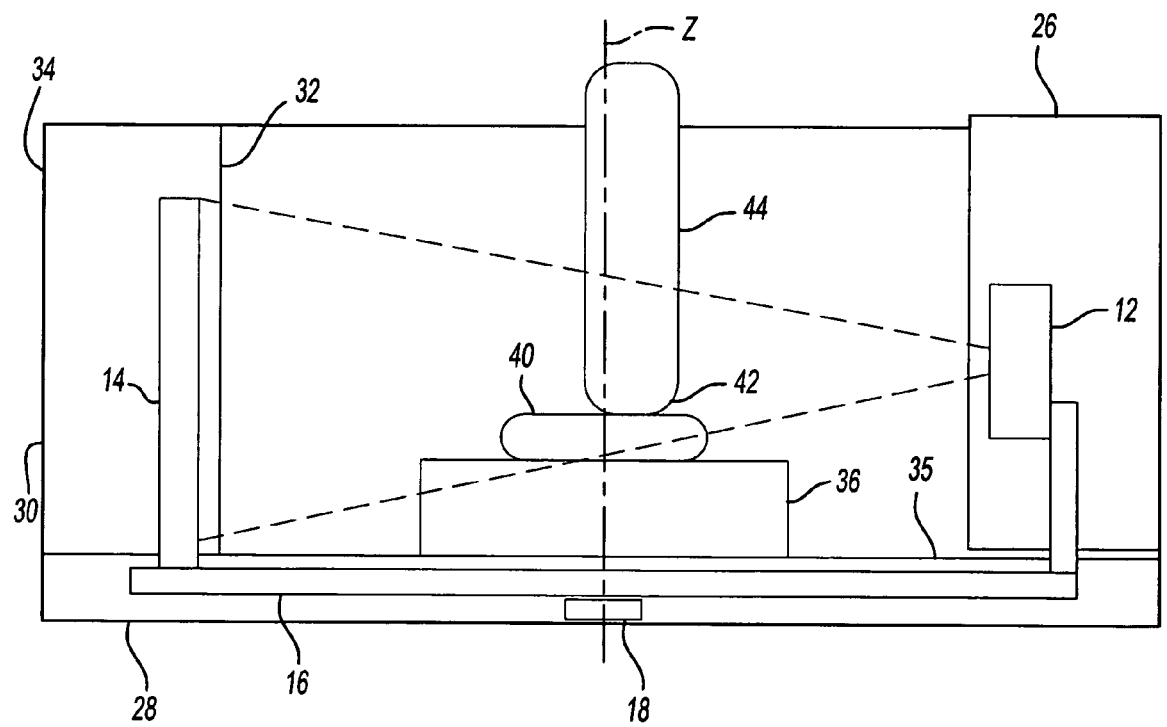

A CT scanning system 10 according to one embodiment of the present invention is shown schematically in FIG. 1. The CT scanning system 10 includes an X-ray source 12 mounted opposite an X-ray detector 14 on a gantry 16. The X-ray source 12 is preferably a cone-beam X-ray source and the detector 14 is preferably a flat panel detector. The flat panel detector 14 would have a converter for converting X-rays into visible light and an array of photo detectors behind the converter. Any suitable X-ray source 12 and detector 14 could be utilized, as the invention is independent of the specific technology used for the CT scanning system 10. Although not shown, a collimator and other known CT components could also be utilized.

The gantry 16 is rotated about an axis Z by a motor 18 controlled by a computer 20. The computer also controls the X-ray source 12 and receives X-ray images from the detector 14. The computer 20 also includes the CT reconstruction algorithm that converts a plurality of X-ray images received by the detector 14 into a three-dimensional CT image stored in computer 20. The computer 20 then selectively displays the CT image on a display 22.

The gantry 16, source 12, detector 14 and motor 18 are mounted in a housing 26. The housing 26 includes a hollow base 28 that contains the gantry 16. The housing 26 further includes an annular upper portion 30 having an annular inner wall 32 and an annular outer wall 34. The source 12 and detector 14 are mounted to rotate about the axis Z between the inner annular wall 32 and the outer annular wall 34. The base 28 includes an upper surface 35 upon which may be supported an optional pedestal 36. The pedestal 36 would be transparent to X-rays.

Figure 2:
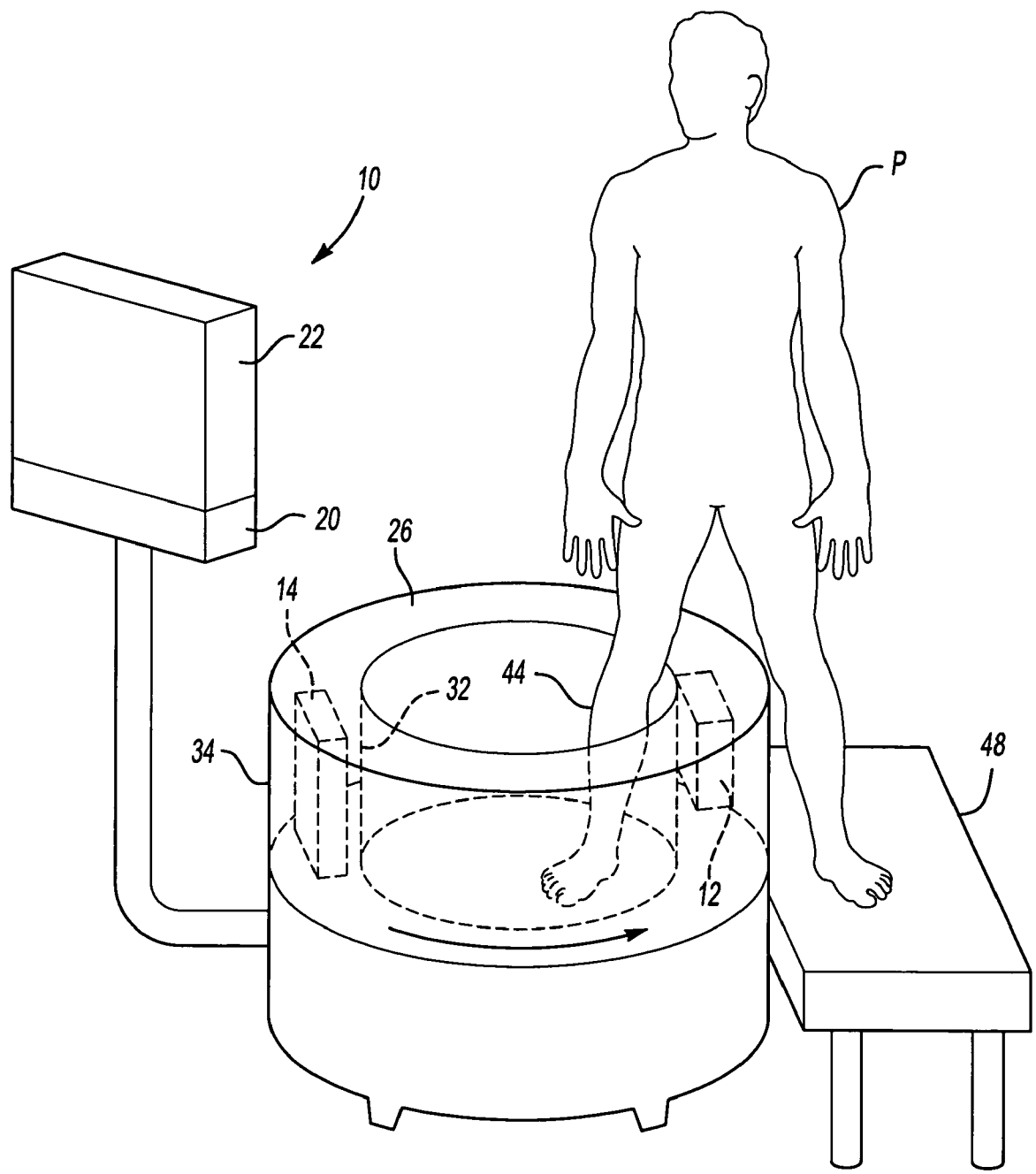
FIG. 2 illustrates a patient using the CT scanning system of FIG. 1 in a standing position.

In use, the patient stands with one foot 40 on the pedestal 36 (or optionally on the upper surface 35 of the base 28) such that the foot 40, ankle 42 and a portion of the lower leg 44 are within the field of view of the source 12 and detector 14. This is shown more clearly in FIG. 2, where the patient P has one leg 44 in the housing 26 and the other leg on an optional outside support surface 48, such as a bench. In this manner, the patient's foot 40, ankle 42 and lower leg 44 can be scanned by the CT scanning system 10 while the patient P is placing weight on the foot 40, ankle 42 and lower leg 44.

When the patient is in position, the motor 18 rotatably drives the gantry 16 at least partially about the patient's foot 40, ankle 42 and lower leg 44, while the detector 14 takes a plurality of x-ray images at a plurality of rotational positions. A three-dimensional CT image is then reconstructed from the plurality of x-ray images utilizing known techniques and algorithms. The doctor can then view and manipulate the three-dimensional CT image on the display 22, including taking section views, slices, rotating the CT image, adjusting image properties (contrast, etc) and other known methods.

Figure 3:
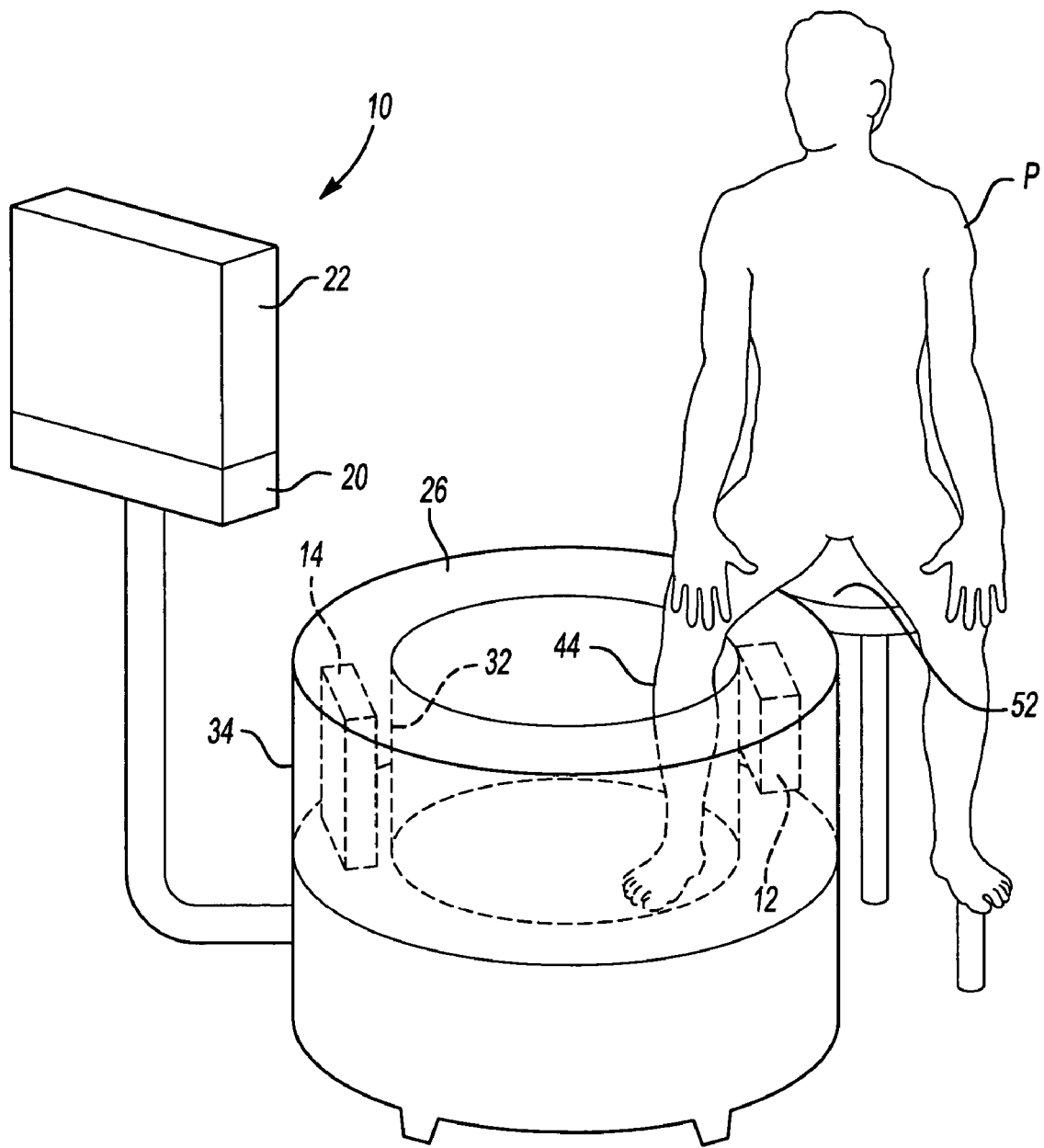
FIG. 3 illustrates a patient using the CT scanning system in a non-weight bearing position.
Figure 4:
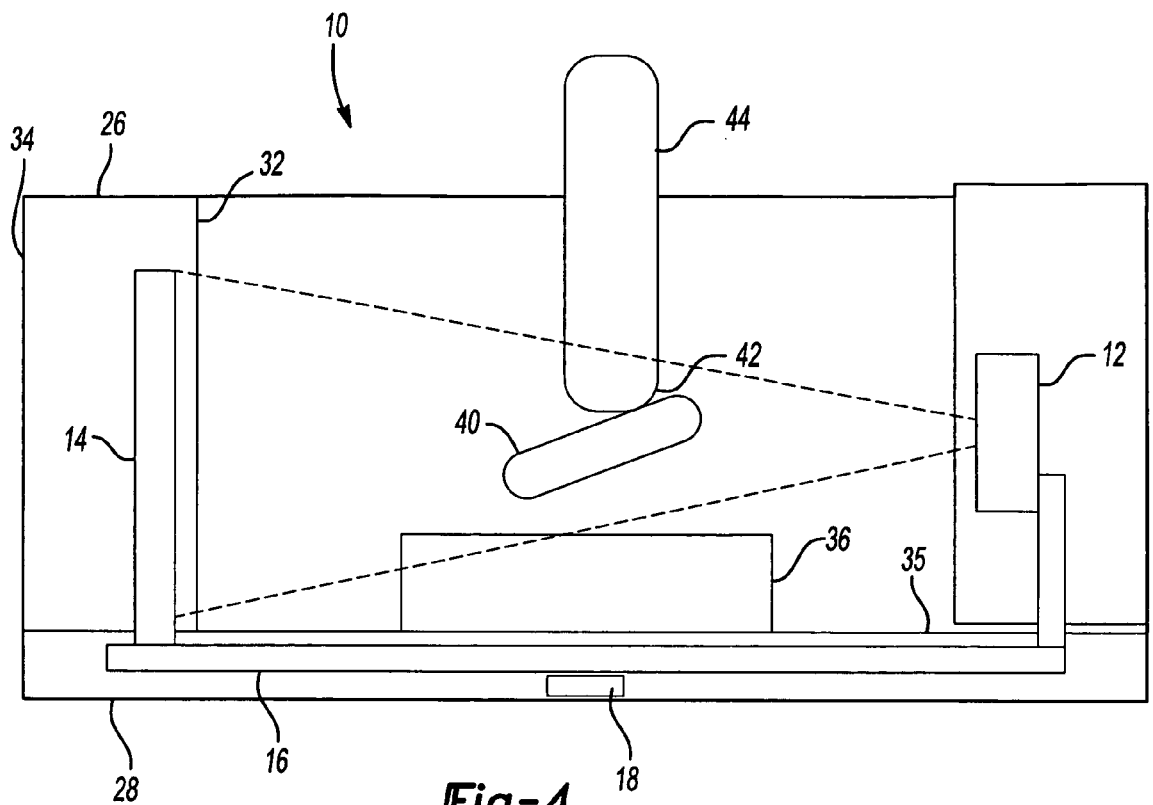
FIG. 4 is a schematic sectional view of the CT scanner and patient's leg of FIG. 3.

The CT scanning system 10 can also be used in a non-load bearing configuration as shown in FIG. 3. The patient P is seated on an adjacent surface 52, such as a stool, with the patient's lower leg 44 inside the housing 26. Referring to FIG. 4, the patient's foot 40 and ankle 42 may be suspended above the pedestal 36 and the upper surface 35 of the base 28 during the scanning. The patient can optionally be scanned in both the load bearing and non-load bearing configurations as the doctor can compare the CT images from both.

Figure 5:
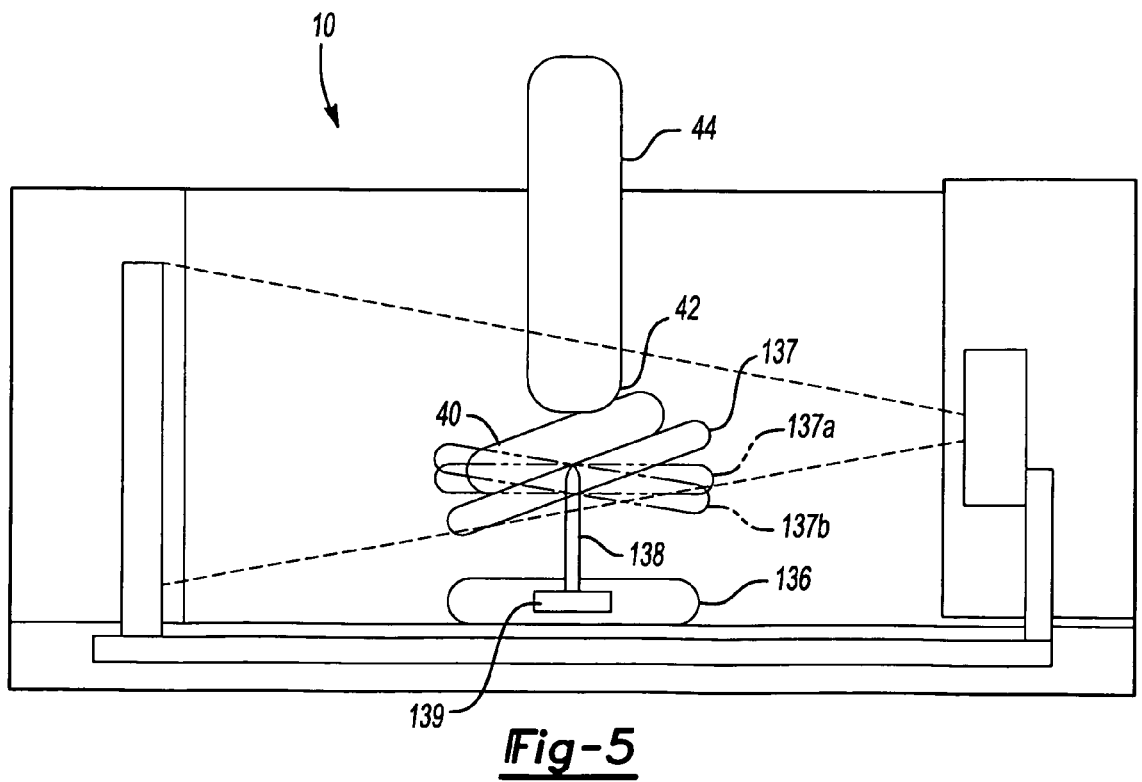
FIG. 5 illustrates the CT scanner with an alternate support for the patient's leg.

FIG. 5 illustrates an alternative support 136 that could be used with the CT scanning system 10 of FIGS. 1-4. The alternative support 136 includes a platform 137 pivotably mounted on a column 138. A motor 139 controls the pivoting position of the platform 137. The platform 137, column 138 and any coupling (not shown) between the motor 139 and the platform 137 are transparent to X-rays. In use, the patient's foot 40 is supported on the platform 137. The motor 139, as controlled by the computer 20 (FIGS. 1-4), then pivots the platform 137 to a plurality of positions 137, 137a, 137b, so that a CT scan of the foot 40, ankle 42 and lower leg 44 is taken in each of the plurality of positions.

In any of the embodiments and configurations of FIGS. 1-5, it may be necessary to ensure proper alignment of the foot 40, ankle 42 and lower leg 44 between the source 12 and detector 14. This can be done with one or more of several alternative ways. First, a laser line pointer between the source 12 and detector 14 can be used for proper placement. One or two scout scans (two-dimensional images) at perpendicular positions) can be taken to verify that the foot 40, ankle 42 and lower leg 44 are in the field of view. A glove or sock into which the foot 40 is inserted can be attached to the pedestal 36 or platform 137 at the proper location. X-ray transparent velco straps can also secure the foot 40 at the proper location. Airbags inflated from the inner annular wall 32 can surround the foot 40 and hold it in the proper location.

Figure 6:
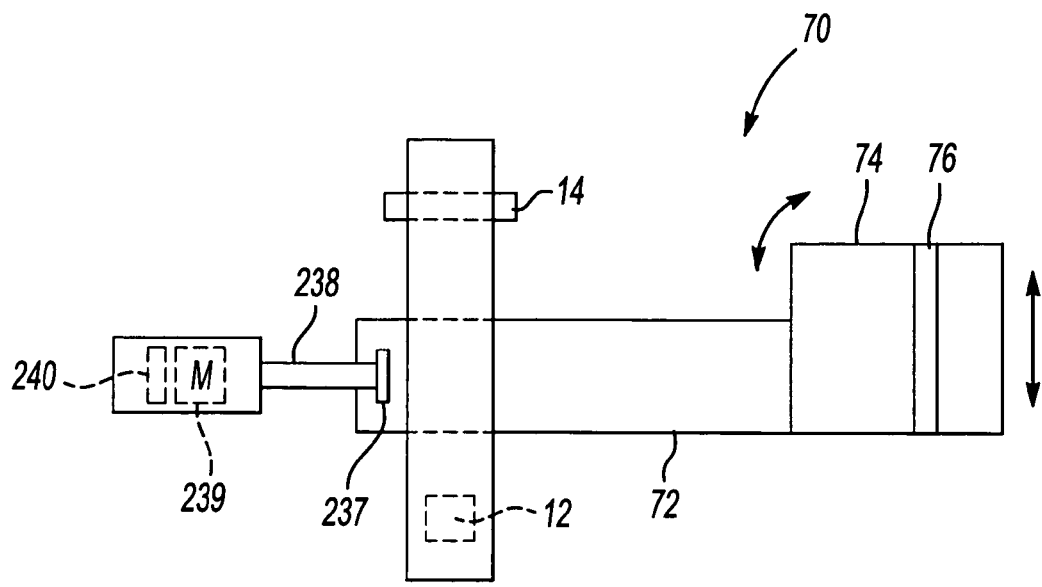
FIG. 6 illustrates an alternate CT scanner.

FIG. 6 illustrates an alternate CT scanner system 70 including the source 12 and detector 14 which are configured and which operate as described above, although oriented to rotated about a horizontal axis. Alternatively, the source 12 and detector 14 could rotate about a tilted axis or even a vertical axis and still be used with the features of this embodiment. The source 12 and detector 14 are rotatable about a portion of a table 72 adjacent a seat 74 having a seat back 76. A strap 78 may optionally help stabilize the patient on the table 72.

The system 70 includes a platform 237 pivotably mounted on an arm 238. The platform 237 can be selectively pivoted to a selected angle relative to the arm 238 and locked in place. A strap 236 may optionally help stabilize a patient's foot 40 on the platform 237. A motor, hydraulic actuator or other loading device 239 controls the load applied to the platform 237 along the axis of the arm 238. An indicator/selector 240 permits an operator to choose and verify the amount of force being applied by the loading device 239. The platform 237, arm 238 and any coupling (not shown) between the arm 238 and the platform 237 are transparent to X-rays.

Figure 7:
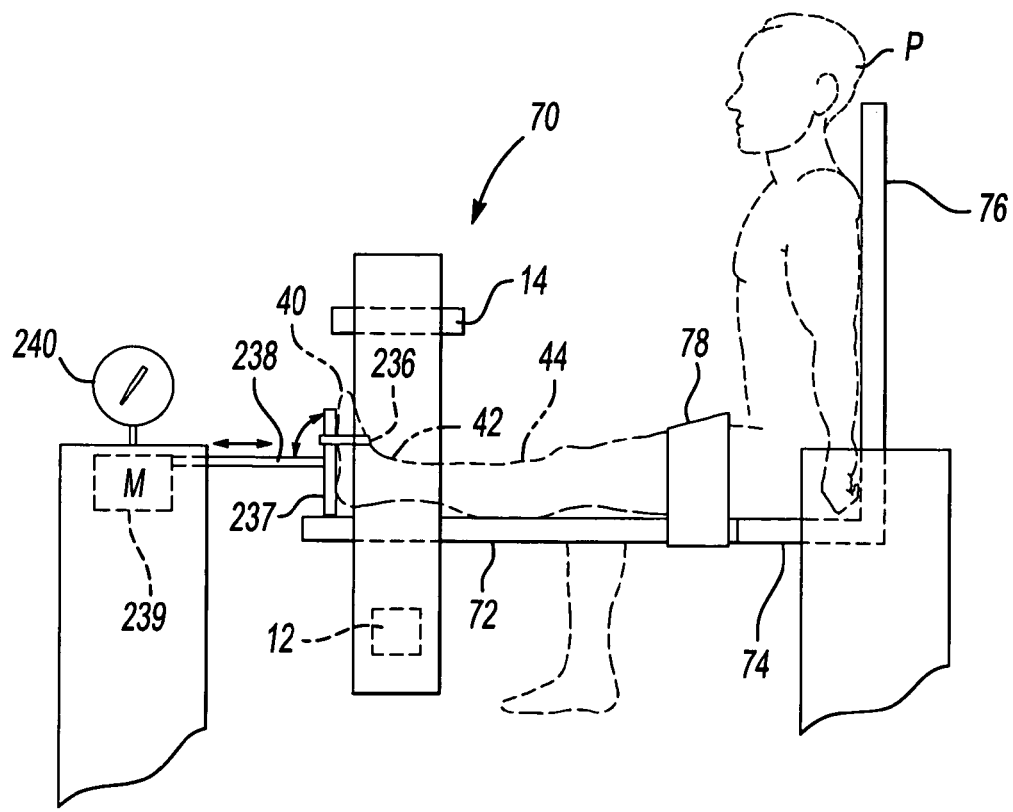
FIG. 7 is a plan view of the CT scanner of FIG. 6.

FIG. 7 is a top view of the system 70 of FIG. 6 (without the patient). Optionally, the seat 74 is movable laterally relative to the table 72, so that the left foot/ankle or right foot/ankle can be scanned easily. Additionally/alternatively, the seat 74 is rotatable (and vertically adjustable) so that the arm or wrist can be placed on the table 72.

In use, the patient's foot 40 is supported on the platform 237 and optionally secured to the platform 237 by the strap 236. The patient sits on the table 72 with the seat back 76 firmly behind the patient. The strap 78 may further stabilize the position of the patient on the table 72. The operator selects an angle of the platform 237 so that the ankle 42 can be imaged in a desired angle. The operator also selects a load to be applied to the foot 40 using the indicator/selector 240. The loading device 239 applies a force via the arm 238 and the platform 237 to the foot 40, ankle 42 and lower leg 44. The source 12 and detector 14 then rotate and perform a CT scan of the foot 40, ankle 42 and lower leg 44, with the foot 40 at the desired angle and with the desired, controlled, constant load (if any) applied.

In accordance with the provisions of the patent statutes and jurisprudence, exemplary configurations described above are considered to represent a preferred embodiment of the invention. However, it should be noted that the invention can be practiced otherwise than as specifically illustrated and described without departing from its spirit or scope.

What is claimed is:

1. A method for scanning a lower extremity including the steps of:
   a) supporting a foot and an ankle of an upright patient on a surface, wherein a first axis is defined between the ankle and a knee of the patient; and
   b) performing a CT scan of the foot or the ankle during said step a) by rotating a gantry about a second axis, wherein the first axis is generally parallel to the second axis.

2. The method of claim 1 wherein said step b) is performed when the patient is applying a load on the foot and the ankle.

3. The method of claim 1 further including the step of adjusting an angle of the surface relative to gravity prior to said step a).

4. The method of claim 3 further including the step of placing the surface at an incline.

5. The method of claim 1 further including the step of rotating an x-ray source and an x-ray detector of the gantry about a vertical axis through the surface during said step b), wherein the second axis is the vertical axis.

6. The method of claim 1 wherein said step b) is performed when the patient is applying no load on the foot and the ankle.

7. The method of claim 1 further including the step of adjusting an angle of the surface relative to a horizontal axis to change an angle of the ankle during said step b).

8. The method of claim 1 wherein the first axis and the second axis are generally vertical.

9. The method of claim 1 wherein the first axis and the second axis are generally horizontal.

10. The method as recited in claim 1 further including the step of securing the foot at a proper location.

11. A method for scanning a lower extremity including the steps of:
   a) applying a load to a patient's foot and an ankle; and
   b) performing a CT scan of the patient's foot or the ankle during said step a).

12. The method of claim 11 wherein said step a) is performed by applying the load in a generally vertical direction.

13. The method of claim 11 wherein said step a) is performed by applying the load in a generally horizontal direction.

14. The method of claim 11 wherein said step a) further includes the step of applying the load to the patient's foot and the ankle with a support surface.

15. The method of claim 14 further including the step of adjusting an angle of the support surface relative to a horizontal axis in order to change an angle of the ankle during said step b).

16. The method of claim 11 further including the steps of supporting the foot and the ankle on a support surface and adjusting an angle of the support surface relative to a horizontal axis prior to said step a).

17. The method of claim 11 wherein a first axis is defined between the patient's ankle and a knee, further including the step of rotating an x-ray source and an x-ray detector about a second axis during said step b), wherein the first axis is generally parallel to the second axis.

18. The method of claim 17 wherein the first axis and the second axis are generally vertical.

19. The method of claim 17 wherein the first axis and the second axis are generally horizontal.

20. The method as recited in claim 11 further including the step of securing the foot at a proper location.

21. A CT scanning system including:
   a support surface to support a lower extremity of a patient, wherein a first axis is defined between an ankle and a knee of the patient; and
   a gantry supporting an x-ray source and an x-ray detector, wherein the gantry is rotatable about a second axis extending transversely through the support surface, wherein the first axis is generally parallel to the second axis.

22. The CT scanning system of claim 21 wherein the support surface is pivotably mounted relative to the second axis.

23. The CT scanning system of claim 21 wherein the second axis is generally perpendicular to the support surface.

24. The CT scanning system of claim 21 wherein the first axis and the second axis are generally vertical.

25. The CT scanning system of claim 21 wherein the first axis and the second axis are generally horizontal.

26. The CT scanning system of claim 21 further including an actuator coupled to the support surface for selectively applying a force to the lower extremity of the patient between the x-ray source and the x-ray detector.

27. The CT scanning system of claim 26 wherein the support surface is between the x-ray source and the x-ray detector.

28. The CT scanning system of claim 21 wherein a load is applied to the lower extremity in a generally vertical direction.

29. The CT scanning system of claim 21 wherein a load is applied to the lower extremity in a generally horizontal direction.

30. The CT scanning system of claim 21 wherein no load is applied to the lower extremity.

31. The CT scanning system as recited in claim 21 further including a fastener that secures a foot at a proper location.

32. A CT scanning system including:
a support surface, wherein the support surface applies a load to a foot and an ankle of a patient; and
a gantry supporting an x-ray source and an x-ray detector, wherein the gantry is rotatable about an axis extending transversely through the support surface to perform a CT scan of the foot or the ankle.

33. The CT scanning system of claim 32 wherein a second axis is defined between the ankle and a knee of the patient, wherein the axis is generally parallel to the second axis.

34. The CT scanning system of claim 33 wherein the axis and the second axis are generally vertical.

35. The CT scanning system of claim 33 wherein the axis and the second axis are generally horizontal.

36. The CT scanning system of claim 32 wherein the support surface is pivotably mounted.

37. The CT scanning system of claim 32 wherein the load is applied in a generally vertical direction.

38. The CT scanning system of claim 32 wherein the load is applied in a generally horizontal direction.

39. The CT scanning system as recited in claim 32 further including a fastener that secures the foot at a proper location.

40. A method for scanning a lower extremity including the steps of:
a) supporting a foot of an upright patient on a surface, wherein an angle is defned between the surface and a horizontal axis;
b) adjusting a position of the surface and varying the angle; and
b) performing a CT scan of the foot or an ankle during said step a) by rotating a gantry about an axis.

41. The method as recited in claim 40 further including the step of securing the foot at a proper location.

42. A CT scanning system including:
an support surface, wherein a foot of a patient rests on the support surface and an angle is defined between the support surface and a horizontal axis, and a position of the support surface is adjustable such that the angle is variable; and
a gantry supporting an x-ray source and an x-ray detector, wherein the gantry is rotatable about an axis extending transversely through the support surface to perform a CT scan of the foot or the ankle.

43. The CT scanning system as recited in claim 42 further including a fastener that secures the foot at a proper location.

* * * * *

UNITED STATES PATENT AND TRADEMARK OFFICE
CERTIFICATE OF CORRECTION

PATENT NO. : 7,394,888 B2  Page 1 of 1
APPLICATION NO. : 11/415856
DATED : July 1, 2008
INVENTOR(S) : Sukovic et al.

It is certified that error appears in the above-identified patent and that said Letters Patent is hereby corrected as shown below:

Claim 40, Column 6, line 21: "b)" should read as --c)--

Signed and Sealed this

Twenty-sixth Day of August, 2008

JON W. DUDAS
*Director of the United States Patent and Trademark Office*